United States Patent [19]

Burzynski

[11] Patent Number: 4,593,038

[45] Date of Patent: Jun. 3, 1986

[54] TOPICAL USE OF 3-PHENYLACETYLAMINO-2,6-PIPERIDINEDIONE FOR TREATMENT OF SKIN WRINKLES AND HYPERPIGMENTATION

[76] Inventor: Stanislaw R. Burzynski, #5 Concord Cir., Houston, Tex. 77024

[21] Appl. No.: 719,522

[22] Filed: Apr. 3, 1985

[51] Int. Cl.⁴ ............................................ A61K 31/445
[52] U.S. Cl. .................................................... 514/328
[58] Field of Search ......................... 546/220; 514/328

[56] References Cited

U.S. PATENT DOCUMENTS 4,470,970  9/1984  Burzynski ............................ 424/177

OTHER PUBLICATIONS

Burzynski, S. R. et al., "Purification, Structure Determination, Synthesis and Animal Toxicity Studies of Antineoplaston A10," 13th *International Congress of Chemotherapy*, (Aug.–Sep. 1983).

Primary Examiner—Leonard Schenkman
Attorney, Agent, or Firm—Arnold, White & Durkee

[57] ABSTRACT

A cosmetic composition is provided which comprises 3-phenylacetylamino-2,6-piperidinedione dispersed in a cosmetically suitable vehicle. This cosmetic composition is useful in the topical cosmetic treatment of skin areas affected with wrinkles or hyperpigmentation.

8 Claims, No Drawings

TOPICAL USE OF 3-PHENYLACETYLAMINO-2,6-PIPERIDINEDIONE FOR TREATMENT OF SKIN WRINKLES AND HYPERPIGMENTATION

BACKGROUND OF THE INVENTION

1. Field of the Invention

The present invention relates generally to cosmetic compositions and their use in reducing wrinkles and spots of hyperpigmentation of the skin. More particularly, the compositions comprise an amino acid derivative, 3-phenylacetylamino-2,6-piperidinedione, in a cosmetically acceptable vehicle.

2. Related Art

Wrinkles are usually a natural consequence of aging. By age twenty-five, a person usually observes some facial wrinkles which accompany cutaneous age-related changes. These changes include loss of subdermal fat, a diminution of muscle tone, and a loss of elasticity. These changes parallel a decrease in collagen and elastin fiber content. Hormonal changes also occur and are linked to a decrease in the water-binding capacity of the skin tissue. In addition to aging, wind, sunlight and disease are among other contributing causes of skin wrinkles. Either singly, on in combination, these forces promote inelasticity and drying of skin tissues.

Hyperpigmentation is generally related to dense melanin concentrations in skin tissues. The color of skin is determined by the amount and size of melanin accumulation. Hyperpigmentation of the skin occurs when there is an increased production of melanin. Spots of hyperpigmentation may result from natural phenomena or they may be caused by external stress, drugs, or other dysfunctions. Most common types of localized hyperpigmentation includes: lentigo, ephelis (freckles), nevus and melasma. The last type corresponds to hyperpigmentation in pregnant women or women taking oral contraceptives and is due to increased level of melanocyte-stimulating hormone and adrenocorticotrophic hormone produced by the pituitary gland.

Historically, the use of cosmetic preparations dates from the teachings of the Egyptian scribes. Herbs and other plant extracts served as the basis of such preparations. In the early 1900's physicians introduced phenol for the treatment of acne. Chemosurgery, or cutaneous peeling, following phenol application became quite popular for the removal of facial wrinkles as well. Techniques of "subdermal filling" also gained acceptance. Paraffin and, later, organosilicone polymers were injected into the skin tissues to "fill out" wrinkles.

Presently, anti-wrinkle preparations are found in a variety of forms including aerosols, foams, lotions, ointments, creams or gels. Lanolins, phospholipids, sterols and fatty acids are common vehicles. An emulsifier is usually included in such preparations to obtain the desired viscosity and stability. Preservatives, such as paraaminobenzoic acid, are also included to prevent contamination.

A variety of cosmetic preparations are currently used. For instance, emollients are generally used to promote skin smoothness. Their topical effect has been attributed to either the prevention of further water loss from the skin or the attraction of water to skin tissues. Hormonal compositions are similarly used to smooth wrinkles. The topical application of certain hormones has been related to the hydration of epidermal cells. Collagen extracts are also currently used to enhance the skin's smoothness. Injected into the dermis, these preparations become vascularized and incorporated into the established collagen network, subsequently replacing the lost fiber.

To enhance even color tone of the skin, cosmetologists have used hydroquinone. Hydroquinone lightens areas of hyperpigmentation.

While topically applied preparations exert short term effects, they generally fail to produce any lasting benefit. Consumers spend millions of dollars for such "anti-wrinkle" preparations annually. The compositions which are injected intradermally do perhaps exert a longer lasting effect, but are expensive and require a physician's skill. It is, therefore, apparent that a cosmetic which is topically applied and long lasting in effect would be most desirable. The present cosmetic compositions provide these features. They are easily applied and have a prolonged effect in reducing wrinkles and spots of hyperpigmentation.

SUMMARY OF THE INVENTION

The present invention in one aspect includes cosmetic compositions containing 3-phenylacetylamino-2,6-piperidinedione in a cosmetically suitable vehicle. The compositions preferably comprise a semi-solid dispersion of 3-phenylacetylamino-2,6-piperidinedione blended in cocoa butter, lanolin, petrolatum or Aquaphor, a mixture of wool-wax alcohols with aliphatic hydrocarbons.

The use of other suitable vehicles is also envisioned. The concentration of 3-phenylacetylamino-2,6-piperidinedione in the compositions is preferably in the range of 1% to 10% by weight.

In another aspect, the invention comprises a method of using the compositions. The compositions are topically applied, preferably in the evening but also can be applied in the morning, to areas of the skin exhibiting pronounced wrinkles and hyperpigmentation. For faster or more comprehensive effect, the topical compositions of 3-N-phenylacetylamino-2,6-piperidinedione can be applied more often throughout the day, such as twice daily. The compositions are applied sparingly and worked into the skin. Their application precludes the need for other skin conditioners. Preliminary clinical studies with these compositions demonstrate a significant reduction in skin wrinkles and lentigo hyperpigmentation with short-term use.

DESCRIPTION OF THE PREFERRED EMBODIMENT

The invention is described below in terms of preferred embodiments known at the time of this application. These embodiments represent the best mode contemplated for preparing the cosmetic compositions and their method of use.

A. Preparation of the Cosmetic Composition

The particular amino acid derivative used in the present compositions, 3-phenylacetylamino-2,6-piperidinedione, may be extracted from natural body fluids or be prepared synthetically by combining the amino acid, L-glutamine, and phenylacetyl chloride. For cosmetic use, the compound ingredient is preferably prepared synthetically as described in prior U.S. Pat. No. 4,470,970 herein incorporated by reference.

The amino acid derivative ingredient is then blended into a proper cosmetic vehicle to produce a semi-solid dispersion. The vehicle can be selected from any of cocoa butter, lanolin, eucerin, petrolatum, or a mixture of wool-wax alcohols with aliphatic hydrocarbons. Other suitable bases will be obvious to persons skilled in the art.

A suitable preservative may also be included in the compositions; methylparaben or propylparaben is preferred for this purpose or paraaminobenzoic acid.

The concentration of 3-phenylacetylamino-2,6-piperidinedione blended in the vehicle usually ranges from one to ten percent by weight.

The following is a particularly preferred formulation of the composition of the present invention.

| Ingredient | Amount |
| --- | --- |
| 1. Lanolin | 10.0 gm |
| 2. Olive Oil | 20.0 gm |
| 3. Eucerin | 10.0 gm |
| 4. Cholesteryl Oleate | 1.5 gm |
| 5. Cocoa Butter | 4.5 gm |
| 6. Lecithin | 2.0 gm |
| 7. Glycol (Ethylglycol) | 8.0 gm |
| 8. Honey | 1.0 gm |
| 9. Lemon juice (Realemon) | 0.5 ml |
| 10. Cetyl Alcohol | 1.5 gm |
| 11. Ethanolamine | 0.5 gm |
| 12. Vitamin A | 50,000 Units |
| 13. Vitamin E | 0.2 mg |
| 14. Vitamin F | 20,000 Units |
| 15. 3-phenylacetylamino-2,6-piperidinedione | 1.0 gm |
| 16. Glycerin | 1.0 gm |
| 17. Rosewater | 3.5 gm |
| 18. Water (distilled water) | 30.0 gm |
| 19. Methylparaben | 1.0 gm |

B. Method of Application of the Cosmetic Composition

To prepare the skin for application of the compositions, a person should thoroughly cleanse the skin using an appropriate cleanser for example, facial soap and warm water.

The cosmetic compositions comprising 3-phenylacetylamino-2,6-piperidinedione in a proper vehicle are applied to the skin in areas of pronounced wrinkling or hyperpigmentation once a day in the morning or twice daily in the morning and evening.

Only a thin film of the compositions is applied to cover the skin. Moisturizers and other skin conditioners can be used when applying the compositions containing 3-phenylacetylamino-2,6-piperidinedione.

EXAMPLE

Experience with the compositions in clinical trial has demonstrated their effectiveness in reducing skin wrinkles on the face and around the eyes. Ten volunteers have used the compositions in an average concentration of two percent. The compositions consisted of 3-phenylacetylamino-2,6-piperidinedione dispersed in a mixture of lanolin, eucerin, olive oil and cocoa butter with 1% of cetyl alcohol and 0.5% triethanolamine as an emulsifier and methylparaben or propylparaben as a preservative. All ten persons observed at least moderate effects within ten to fourteen days. Eight of the people, their age averaging forty to sixty years, were normal healthy individuals; two women had breast cancer. With a single evening application each day, six of the volunteers realized a pronounced reduction in skin wrinkling; four individuals, a moderate effect. Subjects usually observed a decrease in skin wrinkles within five days of initial use of the cosmetic composition.

Two of the volunteers used two different concentrations of 3-phenylacetylamino-2,6-piperidinedione. They found the higher concentrations provide for a more pronounced reduction in skin wrinkles. Specifically, 3-phenylacetylamino-2,6-piperidinedione in concentrations of 4% and 10% produced a greater reduction in skin wrinkling for these two subjects than concentrations of 1% and 2%, respectively.

Two of the volunteers, in addition to noticing a reduction in wrinkling, also observed a decrease in skin hyperpigmentation due to lentigo. Each of these volunteers used 1%, 2% or 4% concentrations once daily for 90 days.

This description of the cosmetic compositions containing 3-phenylacetylamino-2,6-piperidinedione and their use illustrates the invention. Many modifications and changes in the compositions and their methods of preparation and application are feasible without departing from the invention as defined in the claims. For example, the compositions may be applied more or less frequently than once or twice each day. The compositions may include additives such as vitamins, pigments, perfumes, antihistamines, allantoin or honey.

What is claimed is:

1. A method of cosmetically treating skin to reduce wrinkles which comprises topically applying to affected skin areas a cosmetically effective amount of 3-phenylacetylamino-2,6-piperidinedione dispersed in a suitable cosmetic vehicle.

2. The method of claim 1 which comprises the treatment performed twice daily, once in the morning and once in the evening.

3. The method of claim 1 wherein the concentration of 3-phenylacetylamino-2,6-piperidinedione ranges from about one to about ten percent by weight of the total composition.

4. A method of cosmetically treating skin to reduce hyperpigmentation which comprises topically applying to affected skin areas a cosmetically effective amount of 3-phenylacetylamino-2,6-piperidinedione dispersed in a suitable cosmetic vehicle.

5. The method of claim 4 which comprises the treatment performed twice daily, once in the morning and once in the evening.

6. The method of claim 4 wherein the concentration of 3-phenylacetylamino-2,6-piperidinedione ranges from about one to about ten percent by weight of the total composition.

7. A cosmetic composition for treating wrinkles or hyperpigmentation comprising a cosmetically effective amount of 3-phenylacetylamino-2,6-piperidinedione dispersed in a cosmetically suitable vehicle selected from the group consisting of cocoa butter, lanolin, eucerin, petrolatum, or mixtures of wool-wax alcohols with aliphatic hydrocarbons.

8. A cosmetic composition for treating wrinkles or hyperpigmentation comprising a cosmetically effective amount of 3-phenylacetylamino-2,6-piperidinedione dispersed in a cosmetically suitable vehicle selected from the group consisting of cocoa butter, lanolin, eucerin, petrolatum, or mixtures of wool-wx alcohols with aliphatic hydrocarbons, the concentration of 3-phenylacetylamino-2,6-piperidinedione ranging from about one to about ten percent by weight of the composition.

* * * * *